(12) United States Patent
Muse et al.

(10) Patent No.: US 6,601,488 B1
(45) Date of Patent: Aug. 5, 2003

(54) CUTTER ASSEMBLY FOR A MICROSCOPE AND RELATED METHOD

(75) Inventors: Richard R. Muse, Georgetown, KY (US); Lisa J. Vaillancourt, Lexington, KY (US); William J. Young, Lancaster, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/564,970

(22) Filed: May 4, 2000

Related U.S. Application Data
(60) Provisional application No. 60/134,007, filed on May 7, 1999.

(51) Int. Cl.[7] .................. B26D 7/00; B26D 5/02; A61B 17/32; G02B 21/26
(52) U.S. Cl. .................. 83/13; 83/171; 83/915.5; 606/167; 359/391
(58) Field of Search ............. 83/13, 521, 171, 83/915.5; 359/368, 391, 393, 896; 74/469, 471 R; 606/167, 166

(56) References Cited

U.S. PATENT DOCUMENTS

| | | | | |
|---|---|---|---|---|
| 979,333 A | | 12/1910 | Poe | |
| 1,828,460 A | * | 10/1931 | Emerson | 359/391 |
| 1,859,823 A | * | 5/1932 | Fitz | 359/391 |
| 2,857,808 A | * | 10/1958 | Hastings | 310/306 |
| 3,060,781 A | * | 10/1962 | Villalobos | 83/915.5 X |
| 3,179,260 A | * | 4/1965 | Ferlen | 414/7 |
| 3,377,898 A | | 4/1968 | Persson | |
| 3,438,690 A | * | 4/1969 | Skerman | 359/391 |
| 3,489,027 A | * | 1/1970 | Christy | 74/471 R |
| 4,377,958 A | * | 3/1983 | Leighton | 83/410.7 |
| 4,386,602 A | * | 6/1983 | Sheldon et al. | 600/102 |
| 4,498,451 A | * | 2/1985 | Beltz et al. | 125/23.01 |
| 4,511,224 A | * | 4/1985 | Sitte et al. | 269/11 |
| 4,532,838 A | * | 8/1985 | Soderkvist | 83/13 |
| 5,067,382 A | * | 11/1991 | Zimmerman et al. | 83/879 |
| 5,174,188 A | * | 12/1992 | Petroz | 83/882 |
| 5,267,497 A | | 12/1993 | Arens | |
| 5,308,355 A | * | 5/1994 | Dybbs | 606/166 |
| 5,355,755 A | | 10/1994 | Sakata | |
| 5,447,517 A | * | 9/1995 | Steen et al. | 606/167 |
| 5,574,594 A | | 11/1996 | Fowler et al. | |
| 5,715,082 A | | 2/1998 | Saccomanno et al. | |
| 5,906,148 A | * | 5/1999 | Aihara et al. | 83/72 |
| 5,964,716 A | * | 10/1999 | Gregoire et al. | 600/564 |
| 6,132,446 A | * | 10/2000 | Hellenkamp et al. | 606/166 |
| 6,338,291 B1 | * | 1/2002 | Fasanella et al. | 83/171 |
| 2001/0035083 A1 | * | 11/2001 | Fasanella et al. | 83/881 |

\* cited by examiner

Primary Examiner—Boyer D. Ashley
(74) Attorney, Agent, or Firm—King & Schickli, PLLC

(57) ABSTRACT

A low-profile cutter assembly for use on a microscope and related cutting method are provided. The cutter assembly includes a support subassembly having a mounting ring for receiving and engaging the objective of a microscope. A cutter subassembly carried by the support subassembly is displaceable between a home and a forward position in response to actuation. Upon reaching the forward position, additional actuation causes the front end of the cutter subassembly to pivot toward the stage, thereby placing a cutter adjacent to or in contact with the specimen. By selectively actuating the cutter subassembly, multiple cuts may be performed, as necessary or desired for cutting a spore or isolating a particular specimen.

14 Claims, 6 Drawing Sheets

CUTTER ASSEMBLY FOR A MICROSCOPE AND RELATED METHOD

This application claims priority from U.S. Provisional Patent Application Ser. No. 60/134,007, filed May 7, 1999, entitled "Mechanical Spore Cutter Assembly for a Microscope."

TECHNICAL FIELD

The present invention relates to the microscope art and, more particularly, to an improved low-profile cutter assembly for use on a microscope.

BACKGROUND OF THE INVENTION

When viewing a specimen on the stage of a microscope, isolating a single cell or cutting a spore is sometimes necessary. However, as should be recognized, using a conventional knife or scalpel to make the delicate, precise cut required is difficult. This is especially true when very small or even microscopic specimens are presented, which are susceptible to loss or destruction if the cutting operation is improperly performed.

To solve this problem, others in the past have proposed remotely actuated cutter devices for mounting directly to the microscope. One popular form of such a device was developed by Dr. J. R. Raper of Harvard University in the early 1960's. Dr. Raper's cutter device includes a mounting ring for attachment to the objective of the microscope and a downwardly depending fixed-height arm having a yoke for receiving and supporting a pivotally mounted cutter blade. A cable actuator extends through a passage in the mounting ring and attaches to the pivoting blade. Upon actuating the cable, the blade pivots toward the slide, plate, or other specimen present on the microscope stage. Thus, using this cutter device, a cell or spore in the specimen can be easily isolated with a minimum amount of effort.

Although Dr. Raper's cutter device is a great improvement over the manual use of scalpels, knives or the like, some limitations have been observed, especially with the advent of modern, more compact microscopes. More specifically, modern microscopes typically have a much shorter working distance between the objective and the stage than their older counterparts (about 10 millimeters as opposed to 30 millimeters). Thus, Dr. Raper's proposed device, which includes a depending arm having a fixed height of around 30 millimeters, cannot be used in such an arrangement. Absent a complete redesign, this leaves two options: (1) produce a series of specialized cutter devices having different dimensions, each for use on a particular type of microscope; or (2) purchase a special objective of a type known in the art that provides a minimum working distance of about 25 millimeters. Of course, the former option is expensive, as a variety of cutter devices must be kept on hand for use with different types of microscopes. The latter alternative is also expensive and would still be inadequate to accommodate the 30 millimeter depending arm of Dr. Raper's cutter device.

Accordingly, a need is identified for an improved cutter device for use on a microscope that overcomes the above-described limitations. Specifically, the device would be ready for use on many modern microscopes, including those having shorter working distances between the objective and the stage.

SUMMARY OF THE INVENTION

In accordance with the purposes and objectives of this invention, a cutter assembly for use on a microscope is provided. The cutter assembly has a very low profile, but can still supply the cutting force necessary to complete the desired operation smoothly and with a minimum amount of effort. This low profile advantageously permits use of the cutter assembly on a wider variety of modern microscopes than possible with prior art cutter devices, such as the one proposed by Dr. Raper, without the need for extensive retrofitting, adjustment or expense. However, the overall reliability and operational characteristics, including the amount of cutting force supplied, remain uncompromised.

In the preferred embodiment, the cutter assembly includes a support subassembly and a cutter subassembly. The support subassembly includes a forward annular mounting ring having attachment means for securing it to the periphery of the objective. Parallel side wings depend from the support subassembly and include corresponding opposed lateral slots for receiving lugs projecting from both sides of a first member, or cutter body, forming a part of the cutter subassembly. These lugs slide along the slots and allow the cutter subassembly to move between a home and forward position relative to the support subassembly. The forward portion of the cutter body carries a cutter, preferably in the form of a blade or other cutting implement. A separate second member, or connector body, also forms a part of the cutter subassembly. The cutter body pivots relative to the connector body when the cutter subassembly reaches the forward position. As a result of this pivoting, the cutter body moves towards the stage such that the cutter is adjacent to or in contact with the specimen. In the preferred embodiment, this pivoting motion is the result of engagement between corresponding camming surfaces provided on the connector body and the cutter body.

To move the cutter subassembly to and fro between the home position and the forward position, as well as to cause the cutter to pivot toward the stage, an actuator is provided. Preferably, this actuator is in the form of a cable extending through a guide carried by the support subassembly. One end of the cable is attached to the rear end of the connector body. The opposite end preferably includes an enlarged head to facilitate manual or tactile engagement by the microscope user.

To assist the cutter body in pivoting in a controlled fashion relative to the connector body and performing the desired cutting operation upon reaching the forward position, one or more biasing means is provided. More specifically, and in accordance with one preferred embodiment of the present invention, a first biasing means, such as a helical compression spring, connects the cutter body to the connector body. A second biasing means, such as a partially curved plate spring, is positioned between the cutter body and the support subassembly. As will be understood upon reviewing the description that follows, the first and second biasing means together assist in guiding the cutter body as the cutter subassembly is moved to the forward position by the actuator cable and ensure that the desired cutting function is smoothly and reliably provided.

In operation and in accordance with the related cutting method, the actuator cable is pushed through the guide to move the cutter subassembly forward such that the lugs slide forward in the corresponding slots in the support subassembly in a first plane. Upon reaching the terminal ends of these slots, additional pushing on the cable compresses the first biasing means, or helical compression spring, connecting the cutter body and the connector body. The resulting force biases the cutter body toward the home position, which causes the corresponding camming surfaces on the cutter body and connector body to engage each other. As a result of this camming action, the front end of the cutter body pivots toward the stage in a second plane, which places the blade or other cutter adjacent to or in actual contact with the specimen. At the same time, and also as a result of the camming action provided, the rear end of the cutter body pivots upwardly relative to the connector body. The rear end of the cutter body then engages the second biasing means, or plate spring, which in the preferred embodiment is attached to the support subassembly. The biasing force advantageously assists in controlling the pivoting motion of the opposite end of the cutter body toward the stage.

As should now be fully appreciated, one of the significant advantages afforded by the present invention is that the low profile cutter assembly may be used or a modern compound microscope having a shorter working distance between the objective and the stage. Not only does this provide the desired usage that is missing from known prior art cutter devices, but it also avoids the need for special objectives or other expensive and time consuming retrofitting procedures. Despite this low profile design, the cutter assembly can still produce the cutting force necessary to cut a spore or isolate a specimen in an efficient and effective manner.

BRIEF DESCRIPTION OF THE DRAWINGS

The accompanying drawings incorporated in and forming a part of the specification illustrate several aspects of the present invention and, together with the description, serve to explain the principles of the invention.

In the drawings.

Reference will now be made in detail to the present preferred embodiment of the invention, an example of which is illustrated in the accompanying drawing.

DETAILED DESCRIPTION OF THE INVENTION

Figure 1:
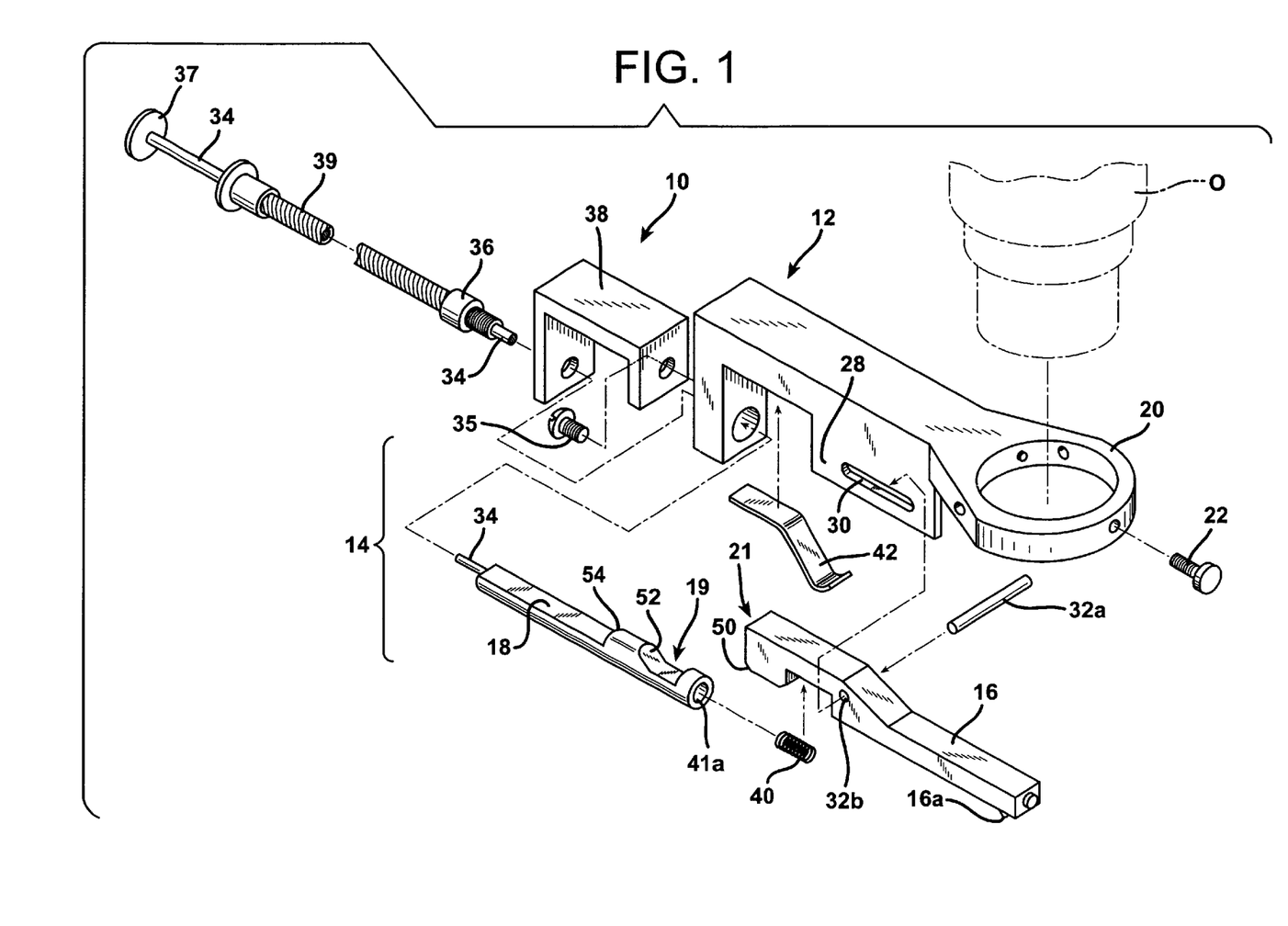
FIG. 1 is an exploded perspective side view showing the various components forming a part of the cutter assembly constructed in accordance with one possible embodiment of the present invention.

Reference is now made to FIG. 1, which is an exploded view that best illustrates the various components forming one particularly preferred embodiment of the improved cutter assembly 10 of the present invention. In this embodiment, the cutter assembly 10 includes a support subassembly 12 and a cutter subassembly 14 (see also FIGS. 2 and 3). The cutter subassembly 14 is slidably carried in a forward portion of the support subassembly 12 and includes a cutter body 16 that interconnects with a separate connector body 18. More specifically, a notch 19 is provided in the forward end of the connector body 18 for receiving a corresponding protrusion 21 on the cutter body 16. As will be further described below, this notch 19 and the corresponding protrusion 21 each include camming surfaces that upon engagement, and in conjunction with biasing means, cause the cutter body 16 to pivot toward the microscope stage S or specimen P in a controlled fashion (see FIG. 5b).

The forward end of the cutter body 16 carries a blade 16a or other form of cutter that provides the desired cutting or isolating function. Preferably, this blade 16a is in the form of a removable, frusto-conical cutter having a circular blade portion (not shown). However, the use of other types of cutters, such as the conventional blade forming a part of Dr. Raper's spore cutter device, is of course also possible. As should be appreciated, since the horizontal axis of cutter body 16 is parallel to the stage (see FIG. 5a), it is preferable to mount the blade 16a at an angle relative to the vertical plane to ensure that it follows an arcuate path and is orthogonal with the stage S upon contacting the specimen P. Of course, the specific angle depends on the distance that the blade 16a travels along the arcuate path (see FIG. 5b).

Figure 2:
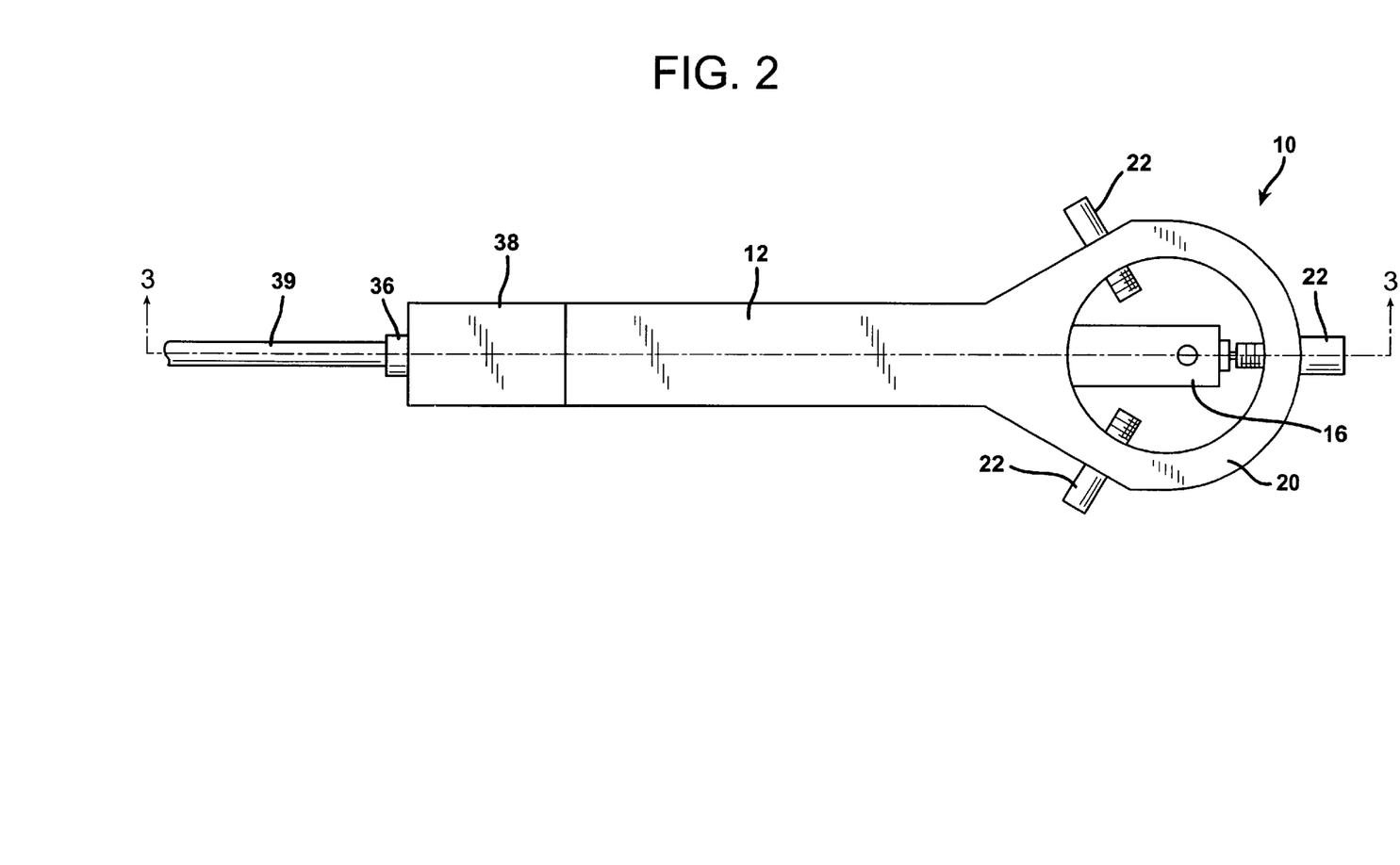
FIG. 2 is a partially cutaway top plan view of the cutter assembly of FIG. 1 once assembled, but apart from a microscope.

As perhaps best illustrated in FIG. 2, a forward mounting ring 20 forms a part of the support subassembly 12. This ring 20 is sized for receiving the microscope objective O. Attachment means are also provided for securing the ring 20 about the periphery of the microscope objective O. The attachment means in the preferred embodiment includes a plurality of thumb screws 22 secured in corresponding, radially extending and circumferentially spaced threaded bores 24 formed in the forward ring 20. Of course, the use of set screws, grub screws, or other equivalent fasteners is also possible, either alone and in combination with a device such as a spring-loaded plunger (not shown) that allows for the cutter assembly 10 to be quickly installed on and removed from the objective without the need for loosening the other threaded fasteners.

Regardless of the particular fasteners or attachment means used, during installation, the forward ring 20 is placed over the lower end of the objective O. Of course, the placement is made so as to not interfere with other structures on the microscope, and is preferably to the side of the objective O. Then, the attachment means, such as thumb screws 22, are actuated or tightened down, as the case may be. In the illustrated embodiment, this tightening action brings the adjacent end of each thumb screw 22 into engagement with the periphery of the objective O, which often is provided with a lip or similar structure that serves as a support ledge. Of course, if no lip or other structure is present, the thumb screws 22 or other fasteners/attachment means are simply tightened until a sufficient holding force is provided against the outer surface of the microscope objective O.

Figure 4:
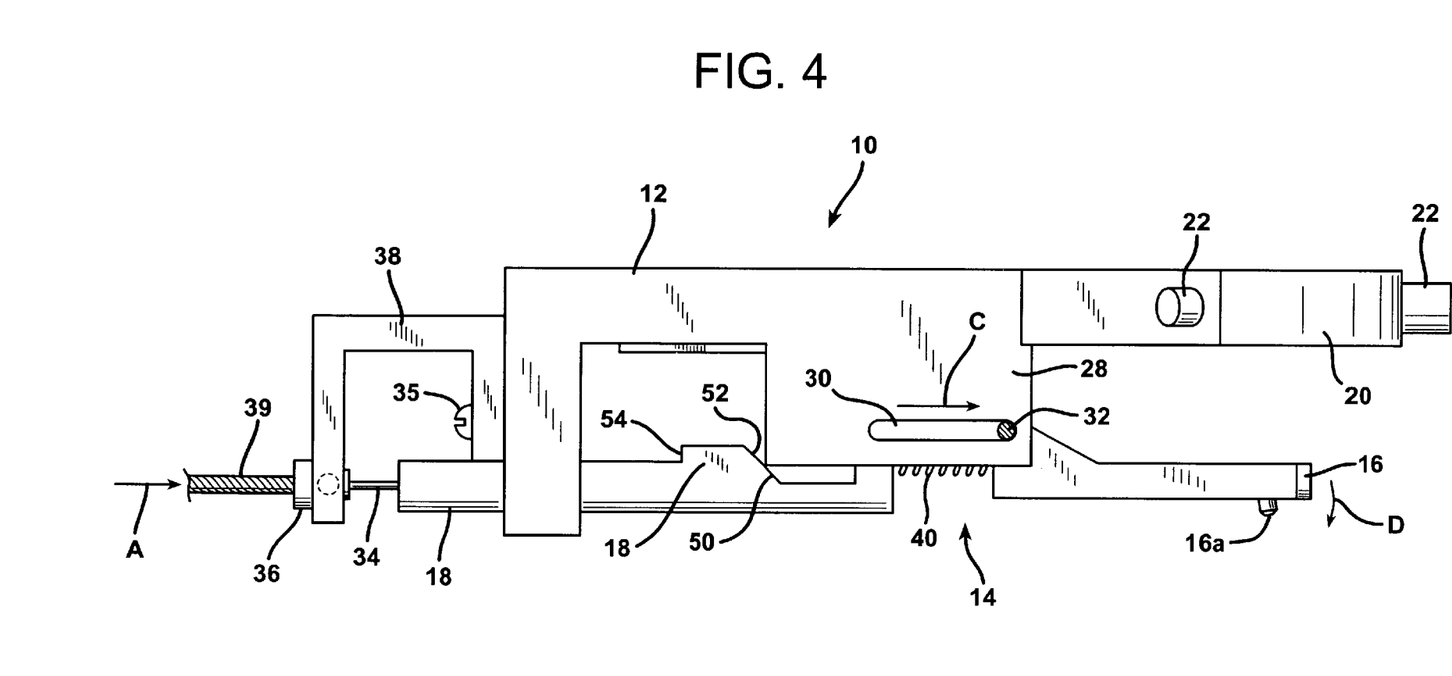
FIG. 4 is a partially cutaway side elevational view of the cutter assembly of FIG. 1.

As also illustrated in FIG. 4, the support subassembly 12 also includes a pair of parallel depending side wings 28 (only one shown in FIG. 1). Each opposing wing 28 includes an aligned lateral slot 30. These slots 30 are elongated and adapted for receiving lugs 32 projecting from each respective lateral side face of the cutter body 16 (compare FIG. 1 with FIGS. 5a and 5b). Preferably, the lugs 32 are non-integrally formed by inserting a transverse pin 32a in a corresponding transverse aperture 32b in the cutter body 16 once in position in the support subassembly 12. Forming the lugs 32 as unitary structures is of course also possible, provided that one of the wings 28 is detachable or the support subassembly 12 otherwise has means for allowing the lugs 32 to enter the slots 30.

An actuator in the form of a cable 34 is fed through a guide 36 carried by an inverted U-shaped guide bracket 38 forming a part of the support subassembly 12. The guide bracket 38 is attached to the forward portion of the support subassembly 12 using attachment means, such as one or more bolts or screws 35, while the cable 34 is attached directly to the rear end of the connector body 18 (see FIGS. 1–3), such as by inserting it in a blind bore having an adjacent set screw (not shown). The actuator cable 34 preferably includes an exposed oversized head portion 37 that facilitates manual or tactile engagement. The downstream portion of the cable 34 between the head 37 and the guide 36 is also preferably covered by a resilient protective sheath 39 that carries a biasing means (not shown) for returning the head 37 to the home position after actuation. Cable actuators, or "triggers," of the type described herein are generally well known in the art, and come in a variety of forms that may also be suitable for use with the present cutter assembly 10. One suitable form is manufactured by Eastman Kodak Co., of Rochester, N.Y.

To assist in guiding the cutter body 16 as it performs the desired cutting function, biasing means are provided. More specifically, a first biasing means, such as helical compression spring 40 extends between the cutter body 16 and the connector body 18. Preferably, both the cutter body 16 and the connector body 18 include opposed aligned bores (see bores 41a, 41b in FIG. 3) for receiving and holding the corresponding ends of the compression spring 40. In addition to this first biasing means, a second biasing means, such as a curved plate or leaf spring 42, is positioned between the cutter body 16 and the support subassembly 12 (see FIG. 2). As will be further understood upon reviewing the description that follows, these biasing means/springs 40, 42 assist in gently moving the cutter body 16 from a home position to the desired pivoted position for cutting or isolating the spore or other specimen, and then assist in reliably returning the cutter body 16 to the home position for re-actuation.

Figure 3:
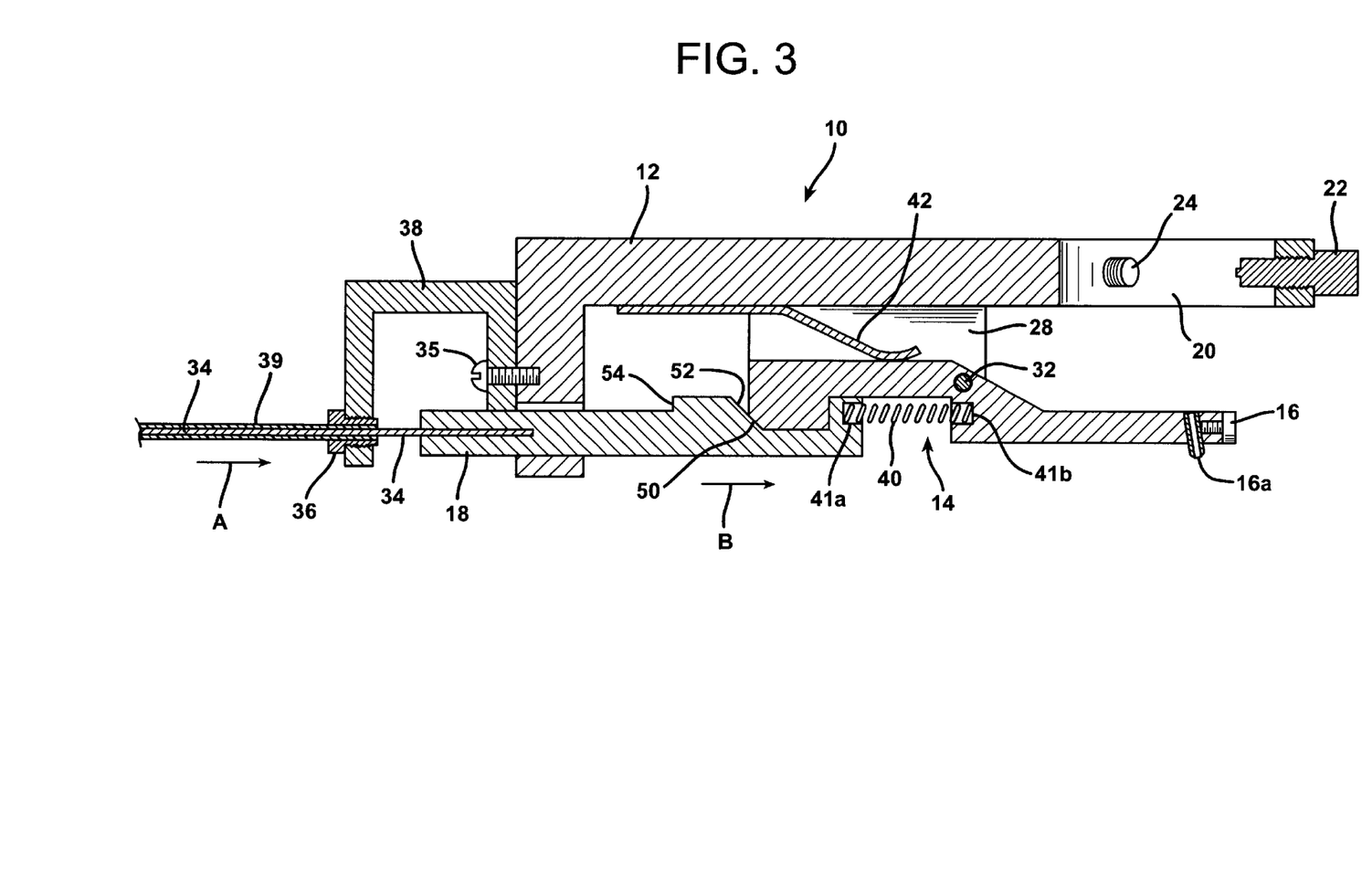
FIG. 3 is a side, partially cross-sectional, partially cutaway view along line 3—3 of FIG. 2.
Figure 5A:
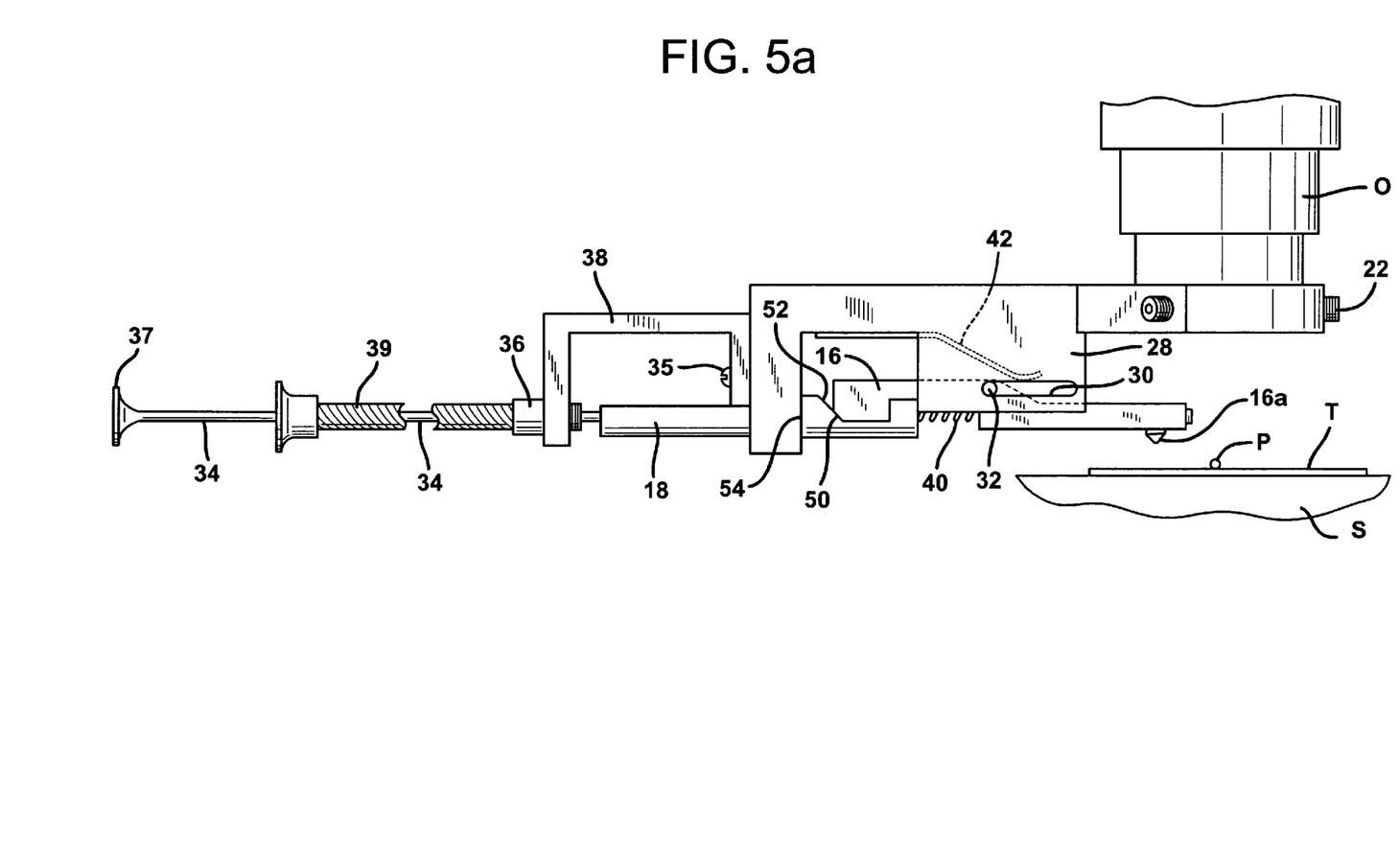
FIGS. 5a and 5b are progressive side elevational views showing the operation of the cutter assembly of the present invention when mounted to the objective of a microscope.
Figure 5B:
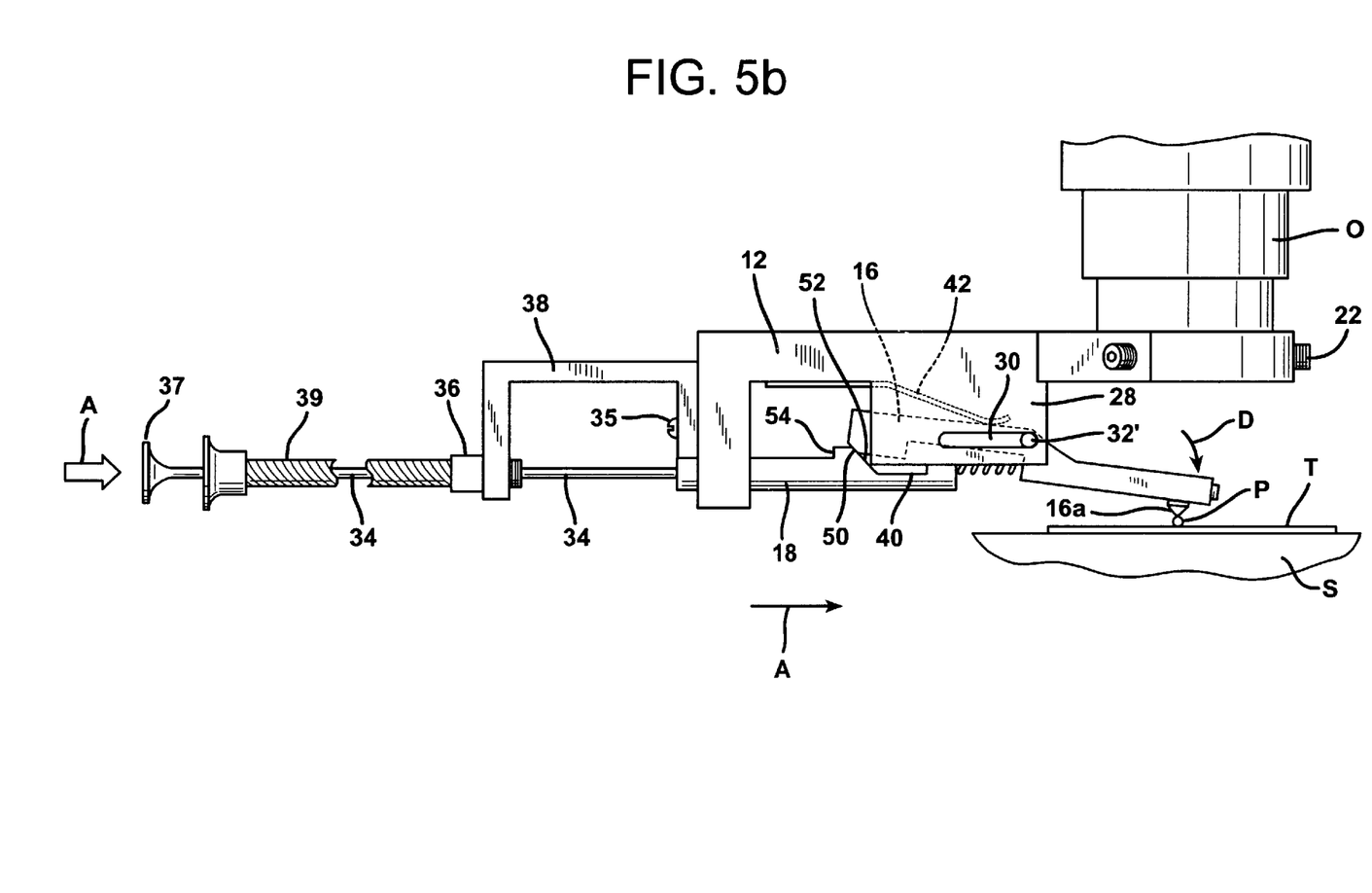

In operation, and with specific reference to FIGS. 2–4 as well as the progressive views of FIGS. 5a and 5b, the actuator cable 34 is manually pushed through the guide 36 by engaging the head 37. By moving the cable 34 forward, the cutter subassembly 14 likewise moves forward such that the corresponding lugs 32 slide forward in the slots 30 (see action arrow A in FIGS. 3, 4, and 5b). Upon reaching the terminal end of the slots 30 (see action arrows B and C in FIGS. 3 and 4, as well as reference numeral 32' in FIG. 5b), additional pushing on the cable 34 compresses the first biasing means, or compression spring 40, extending between the forward cutter body 16 and the connector body 18. As this occurs, a sloping cam surface 50 at the rear of the cutter body 16 engages a corresponding cam surface 52 of the connector body 18. This engagement forces the cutter body 16 to pivot about the lugs 32, which are prevented from moving forward in the slots 30. As a result, the front end of the cutter body 16 pivots toward the stage S (see action arrow D in FIGS. 4 and 5b and position of cutter body in 16 in FIG. 5b). This pivoting motion places the cutter blade 16a in contact with the specimen P supported on the microscope stage S, usually on a separate slide or other transport medium T. At the same time, the rear end of the cutter body 16 pivots upwardly from the connector body 18 against the underside of the plate spring 42 (see FIG. 5b). As should be appreciated, the pivoting action provided by the sloping camming surfaces 50, 52 in combination with the biasing force provided by the plate spring 42 allows for controlled and extremely stable pivoting action.

Upon releasing the pressure or force manually exerted on the cable 34, the cutter body 16 retracts accordingly as a result of the biasing force supplied by the spring 40, as well as the biasing means in the cable actuator. More specifically, the plate spring 42 pivots the rear end of the cutter body 16 toward the connector body 18 simultaneously as the spring 40 expands and allows the forward end of the cutter body 16 to move away from the stage S. As the cable 34 is released further, the lugs 32 move rearwardly along the slots 30 while the front end of the cutter body 16 pivots upwardly even further and begins to return to the home position. A ledge 54 formed in the rear portion of the connector body 18 engages the support subassembly 12 the bracket 38 and defines the maximum retraction distance of the cutter subassembly 14 (see FIG. 5a).

After the cut is made or other desired operation performed, the cable 34 may be fully released and the cutter body 16 fully retracted from the viewing path of the objective O. Alternatively, the cable 34 may be released only a sufficient amount to cause the cutter body 16 to partially retract from the pivoted position, at which time the cable 34 may be re-actuated to perform another cutting operation. Of course, the degree of actuation or retraction of the cutter body 16 is directly dependent on the actuation force supplied to the cable 34, and thus may be selectively adjusted by manipulation of the head 37 as necessary for a particular application.

Preferably, the components of the cutter assembly 10 of the present invention are formed of inexpensive stainless steel to provide high-strength and superior corrosion resistance. Of course, the use of other materials is possible, including plastics, composites, or the like, especially where there is a need for reducing the weight of the overall cutter assembly 10. Alternatively, components that are subject to contact with the specimen such as the cutter body 16 may be fabricated from corrosion-resistant, inert stainless steel that is easy to sterilize, while the other components may be formed of other inexpensive, lightweight materials.

In summary, a low profile cutter assembly 10 is provided that is particularly useful on modern microscopes having a relatively short working distance between the objective O and the stage S. This low profile advantageously avoids the need for objectives O having special sizes or other criteria, as well as the need for keeping a plurality of different cutter assemblies on hand for use on different types of microscopes. Despite the advantageous low profile design, the cutter assembly 10 can still produce the cutting force necessary to efficiently and effectively isolate a spore or other specimen.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A low profile spore cutter assembly for use on a microscope having an objective and a stage for holding a specimen, comprising:
   a support subassembly for attachment to the objective including a pair of lateral slots;
   a cutter subassembly including a first member having a cutter, a first camming surface, and a pair of opposed transversely projecting lugs that are received in the corresponding lateral slots in said support subassembly;
   said cutter subassembly further including a second member having a second camming surface for engaging said first camming surface, said second member being carried by said support subassembly and capable of moving to and fro;

an actuator for moving said cutter subassembly forward relative to said support subassembly, which concurrently moves said lugs forward in said lateral slots;

whereby when said lugs reach a forward end of said lateral slots, continued forward movement of said cable causes the first and second camming surfaces to engage each other and pivot the first member in a controlled fashion such that said cutter contacts the specimen or other medium held on the stage of the microscope.

2. The cutter assembly according to claim 1, wherein said support subassembly includes an annular opening for receiving the objective.

3. The cutter assembly according to claim 2, wherein said support subassembly is provided with means for engaging the objective, whereby said engaging means assists in anchoring said cutter subassembly to the objective.

4. A method for cutting or isolating a specimen on a microscope stage using the assembly of claim 1.

5. An apparatus for cutting a specimen on a stage of a microscope having an objective, comprising:

a cutting device for positioning adjacent to the stage, said cutting device including a body comprised of at least two interconnected portions that are together displaceable toward and away from the specimen, a first portion of the body carrying a cutter and being capable of pivoting relative to a horizontal plane toward the stage when the body is adjacent the specimen such that the cutter is capable of making contact therewith;

an actuator for displacing the body toward and away from the stage;

wherein the first portion of the body is interconnected to the second portion by a compression spring and includes a first camming surface, said second portion of the body including a second camming surface, whereby upon reaching a maximum forward displacement, the spring is compressed and forces the second camming surface to follow the first camming surface such that the first portion pivots and moves the cutter towards the specimen.

6. A method for cutting a specimen on a microscope stage using the apparatus of claim 5.

7. The apparatus according to claim 5, further including means for assisting in controlling the pivoting movement of the first portion of the body relative to the horizontal plane and toward the stage of the microscope.

8. The apparatus according to claim 5, wherein the cutting device further includes a support having an annular ring defining an opening for receiving the objective.

9. The apparatus according to claim 8, wherein said annular ring is provided with a plurality of set screws for engaging the objective, whereby said screws assist in anchoring the cutting device to the objective.

10. The apparatus according to claim 8, wherein said support includes a pair of side wings having corresponding lateral slots;

said first portion of the body further including a pair of opposed transversely projecting lugs that are slidably received and captured in said lateral slots;

whereby a maximum forward displacement of the body is defined by the engagement of the each lug with a forward end of the corresponding slot.

11. The apparatus according to claim 8, wherein said support includes a rear opening for slidably receiving the second portion of the body.

12. The apparatus according to claim 11, wherein said actuator is a cable attached to the second portion of the body slidably received in the rear opening of the support.

13. A cutter assembly for cutting a specimen positioned on a stage of microscope, comprising:

means for cutting the specimen, means for displacing the cutting means toward and away from the specimen in a horizontal plane;

means for pivoting the cutting means relative to the horizontal plane toward the stage; and means for supporting the cutting means relative to the microscope;

wherein the means for pivoting the cutting means includes a first member carrying the cutter means at one end and having a first camming surface and a second members being interconnected by a compression spring;

the means for displacing the cutting means includes a cable secured to an end of the second member, whereby upon reaching a forward position, the spring is compressed the cause the first camming surface to engage the second camming surface and pivot the cutter toward the stage.

14. The cutter assembly according to claim 13, wherein the means for cutting the specimen comprises a cutter.

* * * * *

UNITED STATES PATENT AND TRADEMARK OFFICE
CERTIFICATE OF CORRECTION

PATENT NO.    : 6,601,488 B1
DATED         : August 5, 2003
INVENTOR(S)   : Richard R. Muse; Lisa J. Vaillancourt and William J. Young It is certified that error appears in the above-identified patent and that said Letters Patent is hereby corrected as shown below:

<u>Column 8,</u>
Line 36, please delete the word "members" and replace with -- member including a second, matching camming surface, said first and second members --

Signed and Sealed this

Thirteenth Day of April, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,601,488 B1
DATED : August 5, 2003
INVENTOR(S) : Richard R. Muse et al.

It is certified that error appears in the above-identified patent and that said Letters Patent is hereby corrected as shown below:

Column 8,
Line 35, please replace "cutter means" with -- cutting means --
Line 43, please replace "cutter" with -- cutting means --.

Signed and Sealed this

Twenty-fourth Day of May, 2005

JON W. DUDAS
*Director of the United States Patent and Trademark Office*